United States Patent
Li et al.

(10) Patent No.: US 11,579,055 B2
(45) Date of Patent: Feb. 14, 2023

(54) FULLY AUTOMATIC TRUE TRIAXIAL TUNNEL AND UNDERGROUND PROJECT MODEL TEST SYSTEM

(71) Applicant: SHANDONG UNIVERSITY, Shandong (CN)

(72) Inventors: Shucai Li, Shandong (CN); Weimin Yang, Shandong (CN); Zongqing Zhou, Shandong (CN); Liping Li, Shandong (CN); Shaoshuai Shi, Shandong (CN); Meixia Wang, Shandong (CN); Shuai Cheng, Shandong (CN); Xuguang Chen, Shandong (CN); Chenglu Gao, Shandong (CN); Cong Liu, Shandong (CN)

(73) Assignee: SHANDONG UNIVERSITY, Shandong (CN)

( * ) Notice: Subject to any disclaimer, the term of this patent is extended or adjusted under 35 U.S.C. 154(b) by 1053 days.

(21) Appl. No.: 16/314,460

(22) PCT Filed: Sep. 28, 2017

(86) PCT No.: PCT/CN2017/103871
§ 371 (c)(1),
(2) Date: Dec. 31, 2018

(87) PCT Pub. No.: WO2019/000677
PCT Pub. Date: Jan. 3, 2019

(65) Prior Publication Data
US 2019/0383714 A1 Dec. 19, 2019

(30) Foreign Application Priority Data
Jun. 28, 2017 (CN) .......................... 201710508257.1

(51) Int. Cl.
*G01N 3/12* (2006.01)
*G01N 3/02* (2006.01)
*G01M 99/00* (2011.01)

(52) U.S. Cl.
CPC ................. *G01N 3/02* (2013.01); *G01N 3/12* (2013.01); *G01N 2203/0019* (2013.01); *G01N 2203/0048* (2013.01); *G01N 2203/0256* (2013.01)

(58) Field of Classification Search
CPC .......... G01N 3/24; G01N 3/38; G01N 33/225; G01N 3/04; G01N 3/36; G01N 15/0826;
(Continued)

(56) References Cited

FOREIGN PATENT DOCUMENTS

| CN | 101285808 A | 10/2008 |
|---|---|---|
| CN | 204064816 U | 12/2014 |

(Continued)

OTHER PUBLICATIONS

Mar. 23, 2018 Written Opinion issued in International Patent Application No. PCT/CN2017/103871.
(Continued)

*Primary Examiner* — Brandi N Hopkins
(74) *Attorney, Agent, or Firm* — Oliff PLC

(57) ABSTRACT

Fully automatic true triaxial tunnel and underground project model test system, including a triaxial loading device for loading model test piece, automatic data collection and analysis device, power system and control system; triaxial loading device includes test bench, vertical loading system, horizontal front and back, and left and right loading systems, and the vertical, horizontal front and back, and left and right loading systems apply three-way pressure to model test body; test bench functions for supporting, fixing, and providing counter-force; automatic data collection and analysis device includes micro optical fiber sensor embedded in
(Continued)

model test piece, optical fiber monitoring system, micro pressure box and strain brick, and can collect multi-field information.

10 Claims, 11 Drawing Sheets

(58) Field of Classification Search
CPC ............ G01N 3/303; G01N 1/28; G01N 3/02; G01N 1/08; G01N 33/00; G01N 3/12; G01N 33/24; G01N 3/064; G01N 3/18; G01N 15/082; G01N 15/0806; G01N 3/08; G01N 3/00; G01N 15/08; G01N 3/10; G01N 3/06; G01N 33/222; G01V 1/00; G01V 99/005; G01D 21/02; G01B 21/32; G01M 13/00; G01M 7/022; G01M 99/00; G01M 10/00; G01M 99/007; G01M 7/08; G09B 25/00; E02D 33/00; E21C 41/01
See application file for complete search history.

(56) References Cited

FOREIGN PATENT DOCUMENTS

| | | | | | |
|---|---|---|---|---|---|
| CN | 105510069 | A | * | 4/2016 | .......... G01M 99/007 |
| CN | 105738216 | A | | 7/2016 | |
| CN | 105974056 | A | | 9/2016 | |
| CN | 106483023 | A | | 3/2017 | |
| CN | 106601111 | A | | 4/2017 | |
| CN | 108007781 | A | * | 5/2018 | ............... G01N 3/10 |
| CN | 108169000 | A | * | 6/2018 | |
| JP | 2012-002554 | A | | 1/2012 | |

OTHER PUBLICATIONS

Mar. 23, 2018 International Search Report issued in International Patent Application No. PCT/CN2017/103871.

* cited by examiner

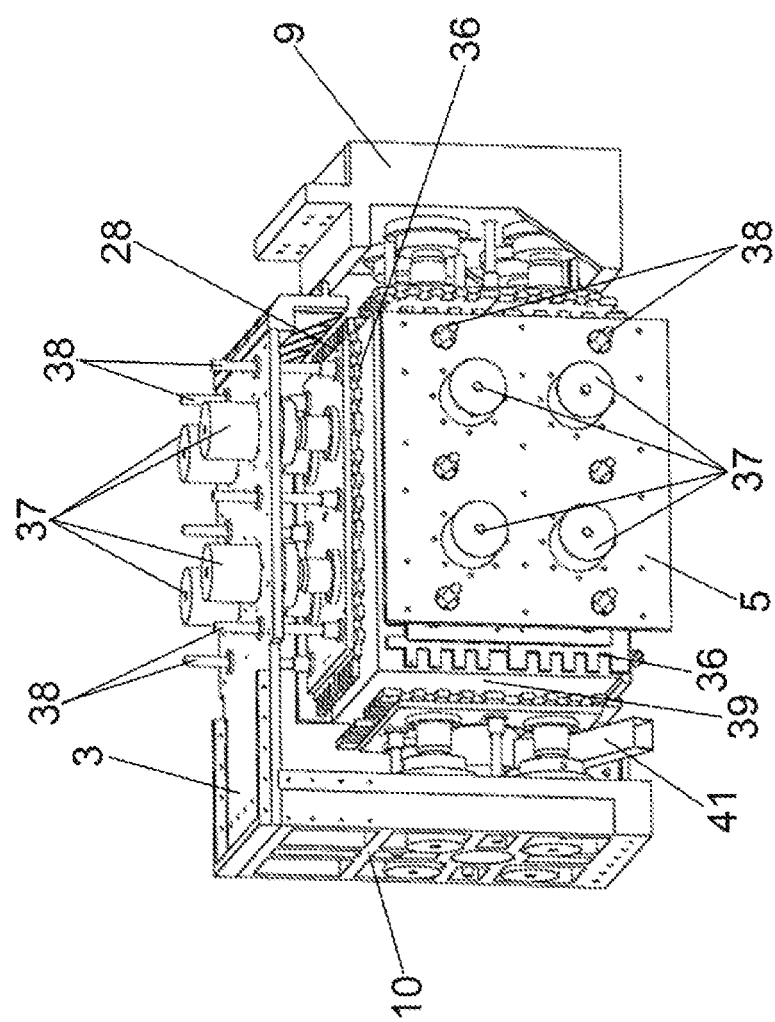

FULLY AUTOMATIC TRUE TRIAXIAL TUNNEL AND UNDERGROUND PROJECT MODEL TEST SYSTEM

FIELD OF THE INVENTION

The present invention discloses a fully automatic true triaxial tunnel and an underground project model test system.

BACKGROUND OF THE INVENTION

With the rapid development of energy engineering and traffic engineering, the number of tunnels and underground projects is increasing and their scale is getting larger and larger, and more and more difficult engineering construction follows. In the construction process of the tunnels and underground projects, faults, caves, underground rivers and other unfavorable geology are often encountered. Due to the physical and chemical effects of the water on the rock, the grades of the surrounding rock of the tunnels suddenly drop, and when the tunnels are constructed to areas of water-bearing masses, the original support design can hardly maintain the stability of the surrounding rock, and the tunnels are prone to collapse and water inrush and mud inrush disasters. The water inrush disaster in the tunnels will cause project delay, damage to mechanical equipment and increase in the investment costs, and also cause a great threat to the safety of onsite construction personnel. Therefore, the identification of the precursor information of water inrush and mud inrush disasters in the tunnels is crucial to the early warning of water inrush and mud inrush in water-rich tunnels and is of great significance for the safe construction of the tunnels and underground projects. Therefore, the research on the mechanical mechanism of power catastrophe of the water-rich tunnels and the description of the evolution process of the water inrush power disasters are crucial.

An underground project model test is an effective method and means for simulating the underground project and guiding the design and construction of the underground project, by means of which the stress states, excavation and support of the protolith in the tunnels and underground projects can be vividly simulated. Since various monitoring elements can be pre-embedded in a test piece, the loading conditions and excavation conditions can be conveniently changed, and the changes of internal stress, strain and other parameters of the test piece are obtained through a monitoring device to provide guidance and reference for the excavation construction of tunnels at the project sites. Therefore, it is of great significance to carry out geomechanical model tests. Domestic and foreign scholars have also developed true triaxial tunnel and underground project model test systems, but the previous true triaxial tunnel and underground project test systems often have the following problems:

(1) A part of the model test systems may cause uneven stress of the test pieces due to the defects of loading devices, and unnecessary shear stress on the surfaces of the test pieces, which affects the accuracy and reliability of the test results.
(2) A part of the model test systems has low loading capacity, such as flexible bladder or hydraulic pillow loading, thereby failing to provide a sufficient load to simulate the high geostress state of deeply buried rock masses.
(3) The model test systems have the disadvantages of being cumbersome, requiring a lot of manpower and material resources, and being unable to achieve automation.
(4) A precursor information monitoring model test system of tunnel water inrush disasters is lacked to clearly clarify the multi-element precursor information of the evolution process of power catastrophe of water inrush of water-rich tunnels and the water inrush disasters.

With the increasing requirements for the scientific research design level and the calculation accuracy of the tunnel and underground project construction, as well as the identification problem and evolution rule of the multi-element precursor information of the water inrush and mud inrush disasters of the tunnels, it is urgent to develop a tunnel and underground project model test system with excellent performance and advanced technology.

SUMMARY OF THE INVENTION

The object of the present invention is to overcome the above-mentioned shortcomings of the prior art, and to provide a fully automatic true triaxial tunnel and underground project model test system in view of the multi-type water inrush precursor information monitoring problem of tunnels so as to enrich the identification problem and evolution rule of the water inrush precursor information of water-rich tunnel, bring effects to practical projects and reduce the losses caused by the tunnel water inrush disasters.

In order to achieve the above object, the present invention adopts the following technical solutions:
A fully automatic true triaxial tunnel and underground project model test system includes a triaxial loading device for loading a model test piece, an automatic data collection and analysis device, a power system and a control system; the triaxial loading device includes a test bench, a vertical loading system, horizontal front and back loading systems and horizontal left and right loading systems, and the vertical, horizontal front and back, and horizontal left and right loading systems apply a three-way pressure to a model test body to better restore the actual stress state of a rock block; and the test bench functions for supporting and fixing, and providing a counter-force;

the automatic data collection and analysis device includes a micro optical fiber sensor embedded in the model test piece, an optical fiber monitoring system, a micro pressure box and a strain brick, and can collect multi-field information such as model stress, displacement, osmotic pressure and the like, and real-time automatic collection of the information is achieved by a computer program, to achieve real-time data entry, analysis, drawing and early warning processing of multi-physical field information; the power system provides required power for the test; and the control system can intelligently control the position and a loading pressure of a loading plate, and meanwhile can control the automatic opening, closing and extension and retraction of a switch door and a bottom plate.

Further, the test bench includes a circular arc-shaped outer bracket, an automatic telescopic base bench and an automatic switch door bracket; and the upper side of the circular arc-shaped outer bracket is connected with the vertical loading system through an upper main plate, and the left and right sides of the circular arc-shaped outer bracket are respectively connected with the horizontal left-right loading system through a left main plate and a right main plate.

The switch door bracket and the circular arc-shaped outer bracket straddle a chassis, a tray is arranged on the chassis, and the tray can ascend and descend, and extend and retract under the driving of a driving device so as to transport the model test piece to a designated position; and the switch door bracket includes a switch door, the switch door can automatically open or close under the driving of a power device, the horizontal front loading system is installed on the switch door, and the switch door is connected with the switch door bracket through the main plate.

Further, the switch door bracket further includes a structural frame, a loading truck and a power device, a slide rail is arranged on the top of the structural frame, and the loading truck is driven by the power device to slide back and forth along the slide rail; the loading truck is connected with the switch door through a connecting piece to drive the switch door to slide back and forth, and the bottom of the switch door is suspended relative to the structural frame; a sensor is installed on the structural frame; and after the test piece is moved into the simulation test device, the sensor sends a signal to a controller, and the controller controls the power device to control the switch door to automatically close.

The loading truck includes a truck body, and the truck body is connected with four rollers through a pulley fixing plate; the pulley fixing plate is used for fixing the rollers and driving the same to move back and forth along the rail without generating a misalignment phenomenon, a reinforcing block is arranged in the truck body, a fixing frame is installed at the bottom of the reinforcing block, and the fixing frame is connected with the switch door.

A groove is formed in the truck body, the reinforcing block is installed in the truck body through the groove, and meanwhile ensures the stability of the loading truck.

The structural frame is a steel structural frame, which has good stability, is used for supporting and fixing the entire switch door system, and has the function of providing a counter-force for the switch door.

The slide rail is a V-shaped slide rail and is connected with the structural frame by a hexagonal cylindrical head screw.

The power device is composed of a left moving oil cylinder, and the oil cylinder has a function of providing long-term power for the loading truck.

Further, the chassis includes a main chassis, two auxiliary chassises and a front extension chassis; the two auxiliary chassises are located on two side faces of the main chassis, and the front extension chassis extends along the axial direction of the main chassis; a loading system is arranged on the main chassis, the loading system can ascend or descend relative to the main chassis under the driving of a lifting oil cylinder, and meanwhile the loading system can achieve coming-in and going-out actions along the slide rail under the driving of a telescopic hydraulic cylinder;

four and one V-shaped guide rails are respectively paved on the two auxiliary chassises and the main chassis for providing rails for the left and right loading systems and the back loading system to load the test body, pulleys and pulley supporting seats are arranged on the V-shaped rails, and the pulley supporting seats are connected with an auxiliary plate of the loading system by bolts for fixing the pulleys to ensure that the pulleys do not shift; and the front extension chassis includes two cover plates and a guide rail fixing plate, and two rows of rollers are fixed on the inner side of the cover plate, and a guide rail reinforcing bracket is connected between the two cover plates to make the overall connection stronger, the guide rail fixing plate is installed at the top of the front extension chassis, the guide rail fixing plate is used for fixing the guide rail, and the loading system can move along the guide rail, and a reinforcing support for locking the loading system is arranged in the side plate.

Further, the loading system includes a tray and a tray bracket, the tray bracket is installed on a side face of the tray, and the tray and the tray bracket are connected by a latch pin, and the tray bracket has a function of stabilizing the tray.

The lifting oil cylinder drives a tray ejecting plate, and the tray ejecting plate drives the tray to move upward; after the tray moves to the set position, the position of the tray ejecting plate is located by a locating seat. The locating seat has a function of fixing the position of the tray ejecting plate, so that the tray ejecting plate does not move, and the lifting oil cylinder provides power for the ejection of the tray.

A roller is also installed on the inner side of the tray ejecting plate, and the tray is placed on the roller of the tray ejecting plate.

Six foot pad brackets are fixed on the lower side of the cover plate, and the foot pad brackets have the function of preventing the deformation of the structure and reinforcing the integrity of the chassis system.

Further, the vertical, horizontal front and back and the horizontal left and right loading systems are respectively composed of a main plate, an auxiliary plate, a pressure plate, four hydraulic jacks and a force guide rod, the loading systems are controlled by five independent control systems and do not influence each other, the loading and unloading of the test body can be completed separately, and the true three-axis is truly simulated; the hydraulic jack and the force guide rod are fixed between the main plate and the auxiliary plate, the force guide rod is composed of high-strength alloy steel for realizing the linear advancement of the loading plate and ensuring the consistency and uniformity of the loading direction. The vertical loading system and the horizontal left and right loading systems have six force guide rods, and the horizontal front and back loading systems have three force guide rods. The pressure plate is made into a zigzag shape, which is a special design for preventing the collision of the loading device, each pressure plate is connected with a displacement meter, the moving distance and position of each loading plate are fed back to a control center in time through a signal transmission device for realizing real-time monitoring of the loading process, and the horizontal back loading system is provided with a tunnel excavation hole.

Further, in the model test body, the test body is a block having a length of 2.5 m, a width of 2 m and a height of 2 m, the test body is in contact with a triaxial pressurization system through the pressure plate, and a plurality of water-bearing masses are arranged in the test body for simulating many types of poor water-bearing masses in a water-rich tunnel, including fault fracture zones, water containing caves, karst pipelines and other types, simulating the catastrophic evolution process of various water inrush types, obtaining the precursor information of different water inrush types, and disclosing different water inrush material energy state transitions and critical characteristics thereof, the model test body can be made in a cast-in-place manner or made by laying prefabricated blocks, a tunnel hole is formed in the middle of the model test body, the maximum diameter of the excavation hole is 200 mm, and an excavation protective cover is arranged at the entrance of the hole for protecting the test system.

Further, the control system is monitored and operated by a computer, the automatic control of the entire test process is achieved by a programming algorithm, the core of the control system is a programmable logic controller (PLC) running on a microcomputer, the execution and operation of various commands are performed by using the PLC, and the automatic operation of the loading modules of the power system and the model test bench is realized by a model test control system running in a CPU. The control system can automatically control an oil pump in the power system, and can also automatically control the main plates, the switch door and the tray of the model test bench, and can perform automatic monitoring and real-time feedback on the position of the tray, the loading positions of the main plates, the positions of the auxiliary plates, the position of the switch door and the pressure magnitude. In a test project, the test bench can be automatically operated by inputting preparatory positions and error values of devices into the equipment, and the positions of the devices and the pressure magnitude can be monitored in real time. The control system includes 7 modules of home page return, manual operation, automatic operation, test parameter adjustment, test operation state monitoring, alarm display and system exit. The manual operation module can adjust the state of the switch door, manually control the ascending, descending, coming-in and going-out states of the tray, and meanwhile can feed back the displayed position and pressure parameters according to the detection. The positions of the loading plates and the required forces to be applied need to be manually filled and set.

In an automatic operation process, the automatic loading module can realize the automatic operation of the test bench by inputting preliminary positions and the error values, monitor the position and pressure parameters of the loading plates in real time and perform window visual dynamic demonstration.

The test parameter adjustment module can achieve multi-stage loading by using test parameter setting and inputting multiple stages of pressure, loading time, pressure holding time and a running switch, thereby meeting the test requirements and being closer to the actual general project situation.

The test operation state monitoring module mainly monitors the positions and pressures in real time. The monitoring data change state can be visually displayed through a dynamic curve, and the current operation situation is displayed by digits to embody the intuitiveness.

The alarm display module provides automatic feedback on safety error items through the recorded equipment operation state, so that the test personnel can conveniently inspect, repair and maintain the equipment.

The triaxial loading device is powered by the power system, the power system is composed of an oil tank, an oil tank cover plate, an oil pipe, an oil pump, a proportional pressure flow control valve, a distribution box, a back closure plate, an upper closure plate, and a right closure plate, the power system is connected with the control system, after the power supply is turned on, the oil pump works to extract the hydraulic oil in the oil tank, the oil is controlled by the proportional pressure flow control valve to enter the hydraulic cylinders to load the test body, and when the test body is unloaded, the hydraulic oil enters the oil tank through the oil pipe.

A use method of the fully automatic true triaxial tunnel and underground project model test system includes the following steps:

1. Opening of the switch door: the device is started, the left moving oil cylinder provides power, and the loading truck moves to drive the front main plate so as to open the switch door of the test system.
2. Transportation of the test body: after the switch door is opened, the tray is removed from the main chassis through the tray ejecting plate so as to move on the pulley, after the control system controls the tray to run to the fixed position of the front extension chassis, the test body is placed and fixed, and then the tray runs to the designated position in the model test system again, and finally the tray drops and is fixed to the main chassis.
3. The application of an initial stress field: after the tray is fixed, the control system controls the hydraulic jacks in three directions to work at the same time to load the test body to simulate the three-way compression of the rock mass.

The initial stress field is applied in a multi-stage loading mode, the pressure stabilization after every stage of loading is controlled by the proportional pressure flow control valve, and the next stage of loading is achieved after meeting the pressure to be maintained so as to achieve the required initial pressure.

4. Excavation of the test body: after the test body arrives at the required initial stress field, the test body is excavated and is slowly excavated at the water bearing mass, and the test phenomenon is observed from time to time.
5. Capture of multi-element precursor information of the water inrush of the tunnel: the multi-element information includes displacement, stress, pressure and the like and is transmitted by a monitoring element to a data analysis system to perform real-time data entry, analysis, and the like.
6. Execution of multiple groups of tests: the water inrush phenomenon of the tunnel is analyzed through multiple groups of test bodies, and the water inrush phenomenon of the water-rich tunnel is quantitatively described in combination with the data of the real-time data collection system, and the precursor information of the water inrush and other rules are summarized through the test phenomenon.

The fully automatic true triaxial tunnel and underground project model test system provided by the present invention has the following advantages:

(1) The model test system is modular and is convenient to assemble, disassemble and transport.
(2) The whole process of the model test is controlled by a computer, automatic operation is achieved, so that the test is simpler and more convenient, the manpower, material resources and financial resources are greatly saved, and the applicability is better.
(3) The model test system adopts the force guide rods, so that the loading is uniform, the stress of the test piece is uniform, the loading accuracy can reach 0.01%, and the test result is more accurate and reliable.
(4) The model test system has better loading capacity and can simulate the stress state of the deeply buried rock mass, and the maximal simulation buried depth can be greater than 3000 m.
(5) The size of the model test body is 1.5×1.0×1.0 m, so that the size is moderate, the model test body can be cast-in-place and can also be prefabricated to achieve repeated tests.
(6) The model test system realizes the simulation of a complex three-dimensional geostress field via discrete multi-principal stress loading, thereby being more related to the actual situation, and the test result has guiding significance.
(7) The test body can simulate a variety of disaster source water types, thereby enriching a variety of water inrush types and water-rich shapes, and the multi-element precursor information of the water inrush disasters under different disaster source forms can be researched.
(8) Through system software control, independent hydraulic loading of each direction of each direction can be achieved.

BRIEF DESCRIPTION OF THE DRAWINGS

The drawings constituting a part of the present application are used for providing further understanding of the present application, and the illustrative embodiments of the present application and the description thereof are used for explaining the present application and do not constitute undue limitations to the present application.

FIGS. 7A and 7B are schematic diagrams of a triaxial loading system in the fully automatic true triaxial tunnel and underground project model test system;

Figure 1:
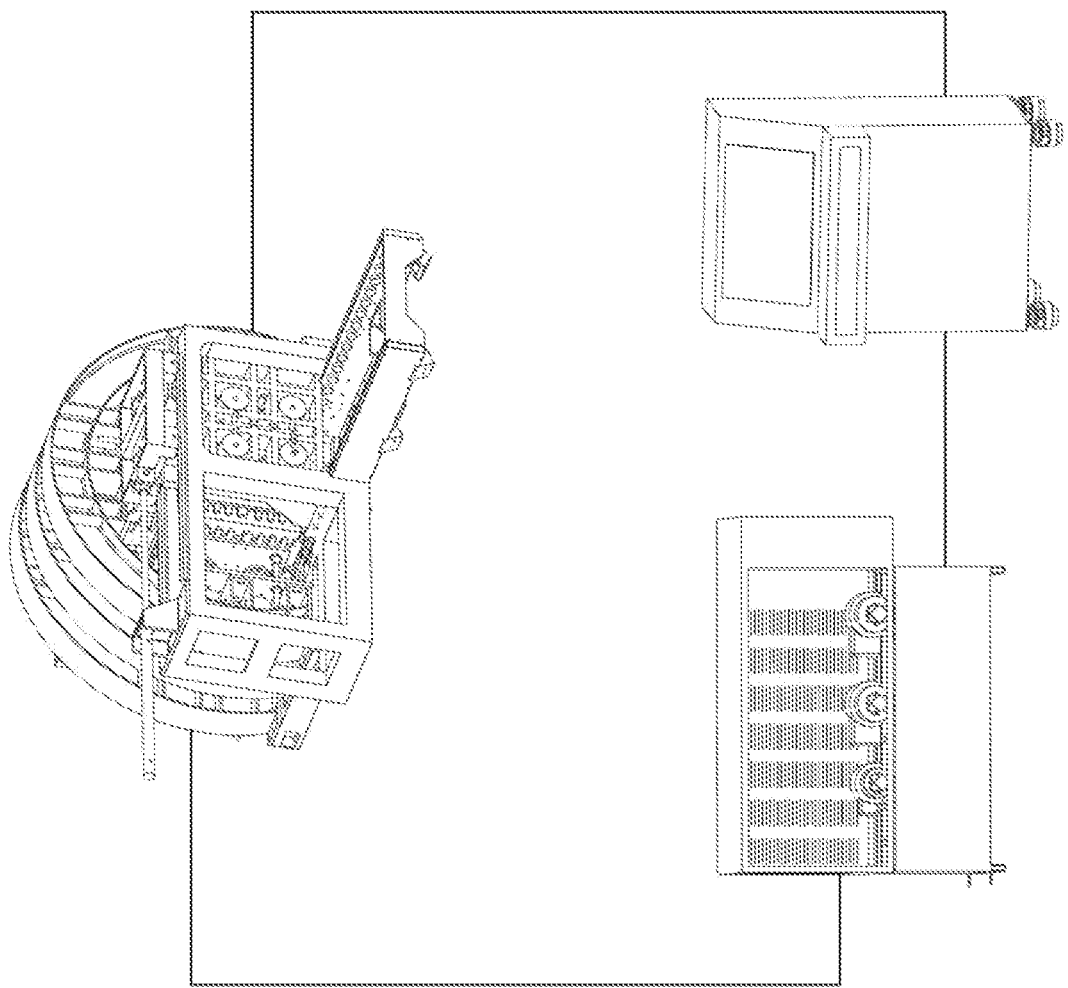
FIG. 1 is a diagram of a fully automatic true triaxial tunnel and underground project model test system.
Figure 2A:
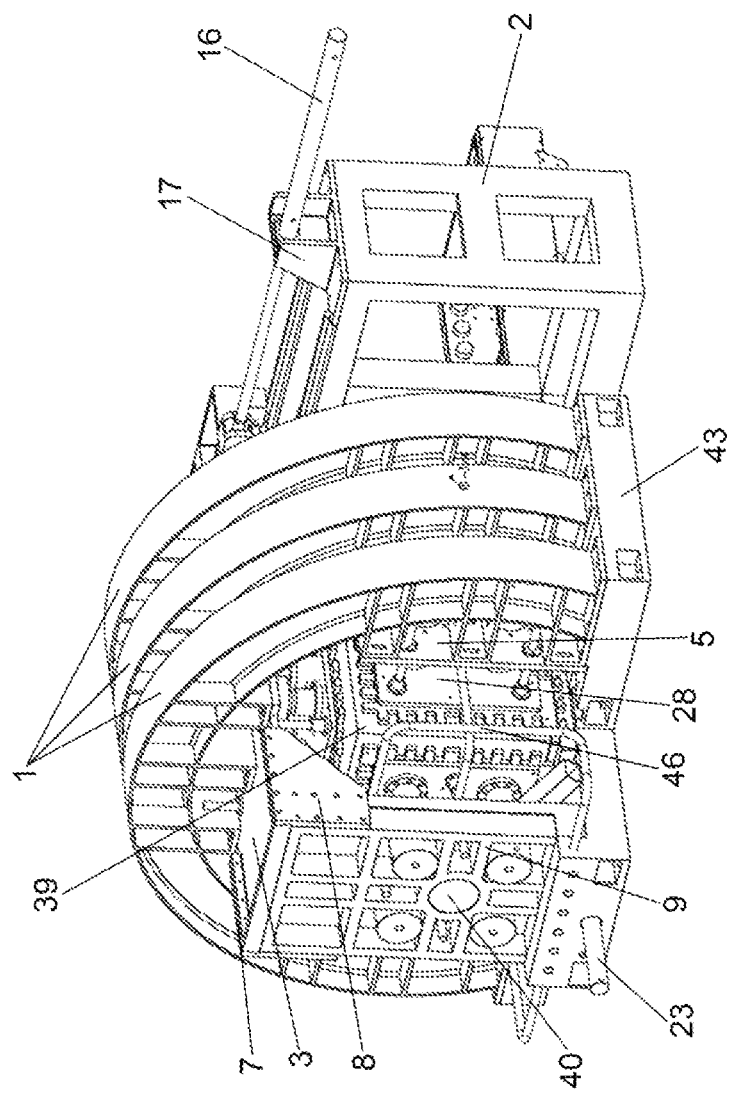
FIGS. 2A and 2B are structural schematic diagrams of a test device in the fully automatic true triaxial tunnel and underground project model test system.
Figure 2B:
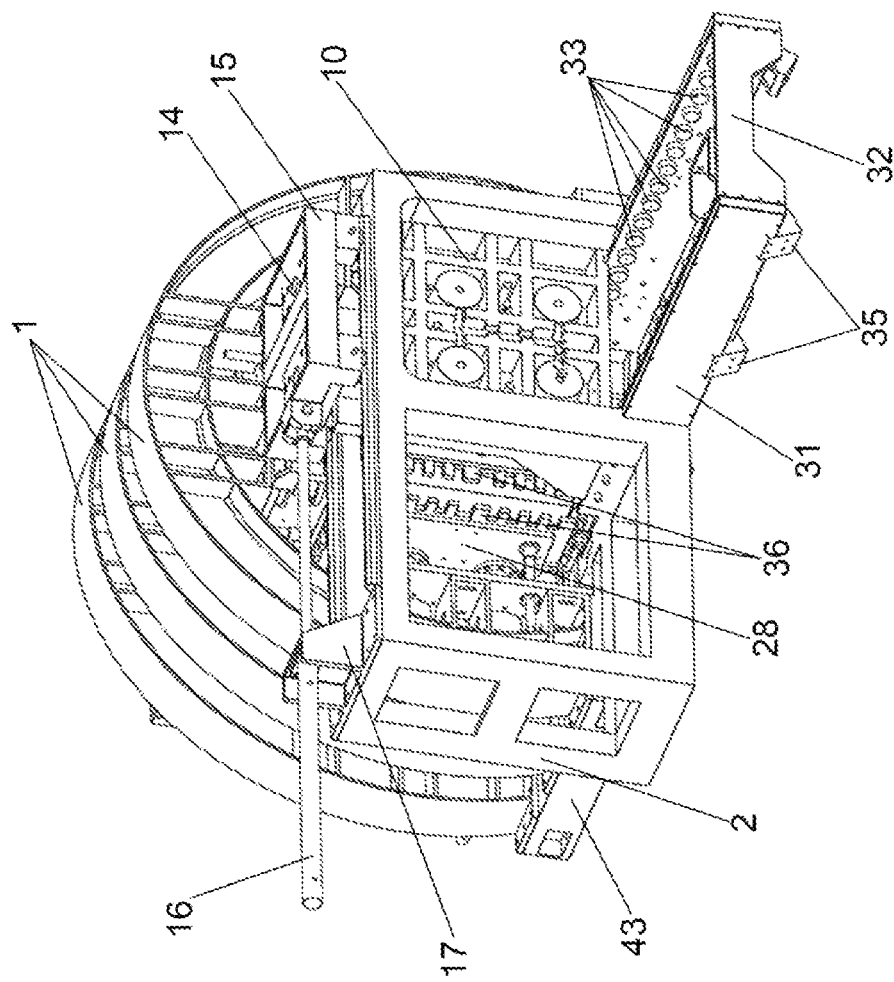
Figure 3:
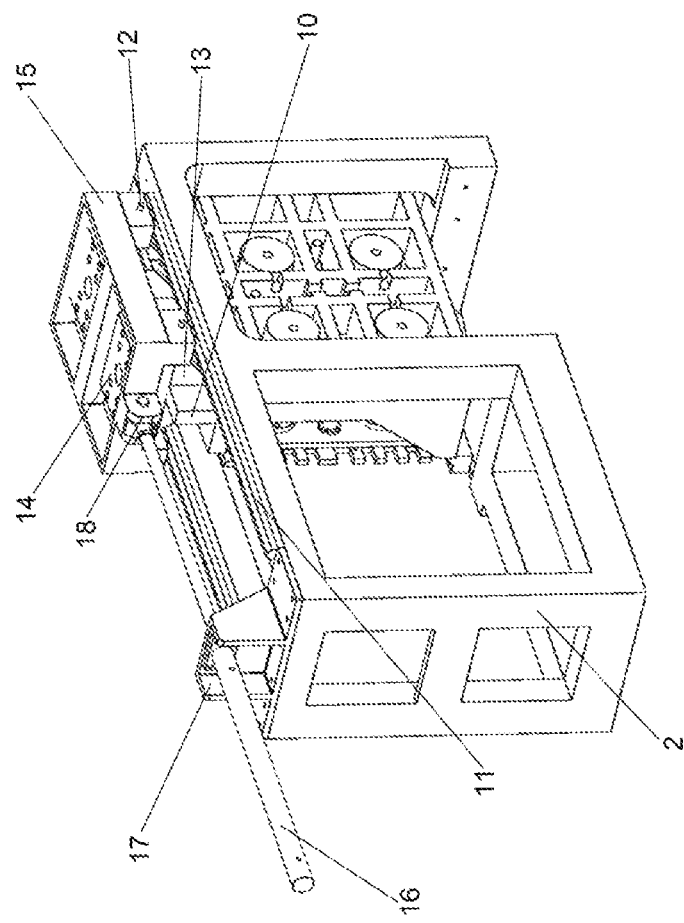
FIG. 3 is a structural schematic diagram of a switch door system in the fully automatic true triaxial tunnel and underground project model test system.
Figure 4:
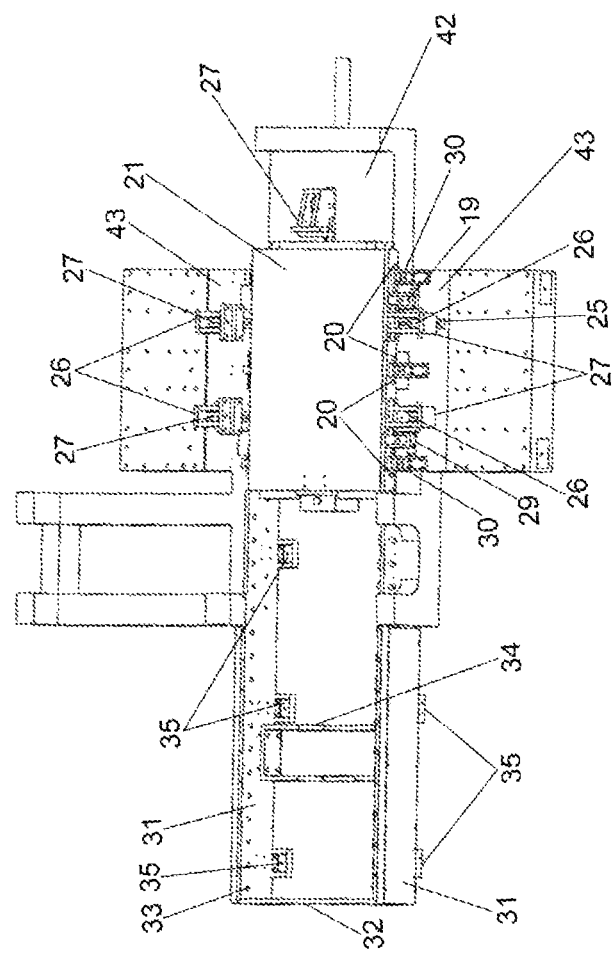
FIG. 4 is a structural schematic diagram of a chassis system in the fully automatic true triaxial tunnel and underground project model test system.
Figure 5:
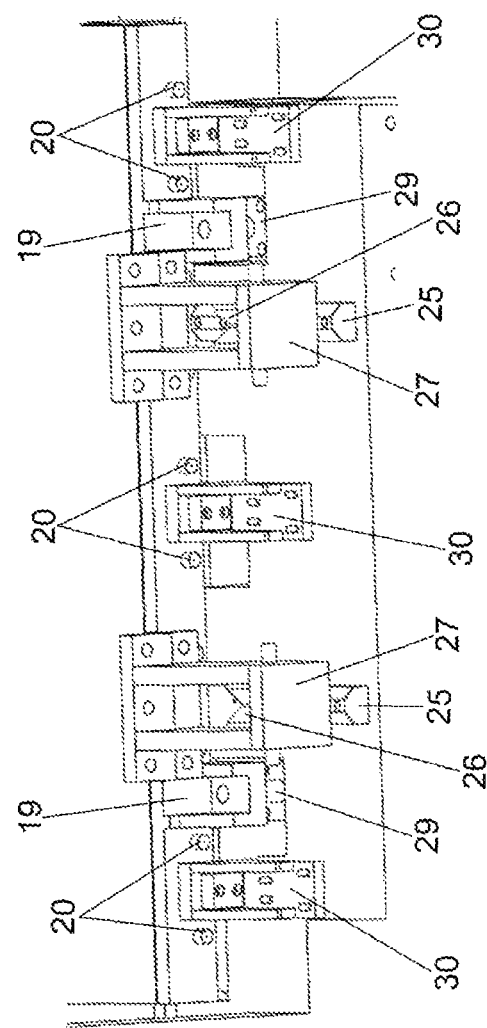
FIG. 5 is a partial enlarged drawing of the chassis system in the fully automatic true triaxial tunnel and underground project model test system.
Figure 6:
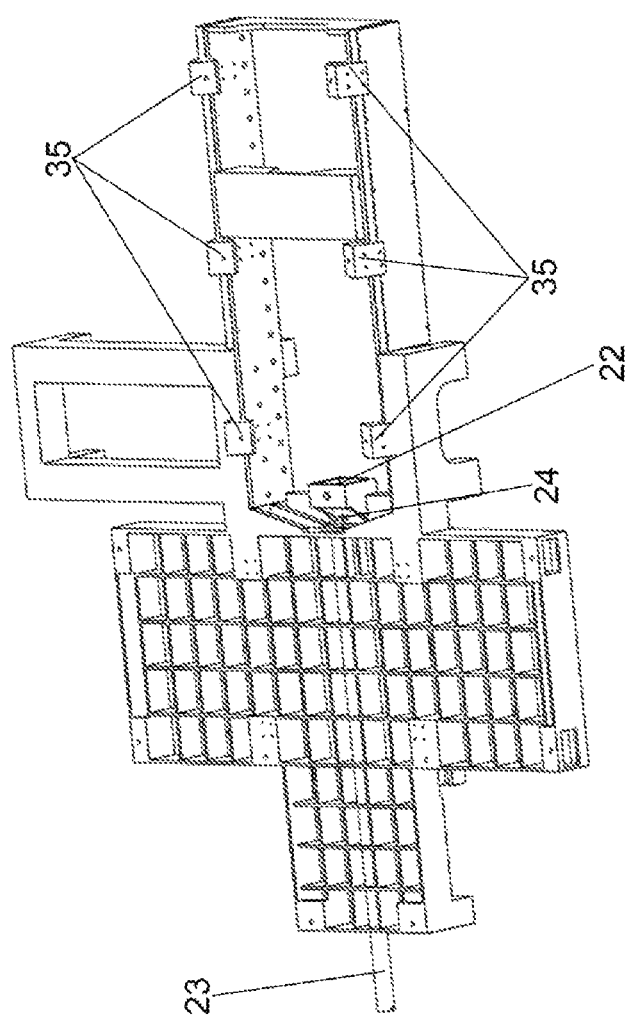
FIG. 6 is a schematic diagram of a bottom structure of the chassis system in the fully automatic true triaxial tunnel and underground project model test system.
Figure 7B:
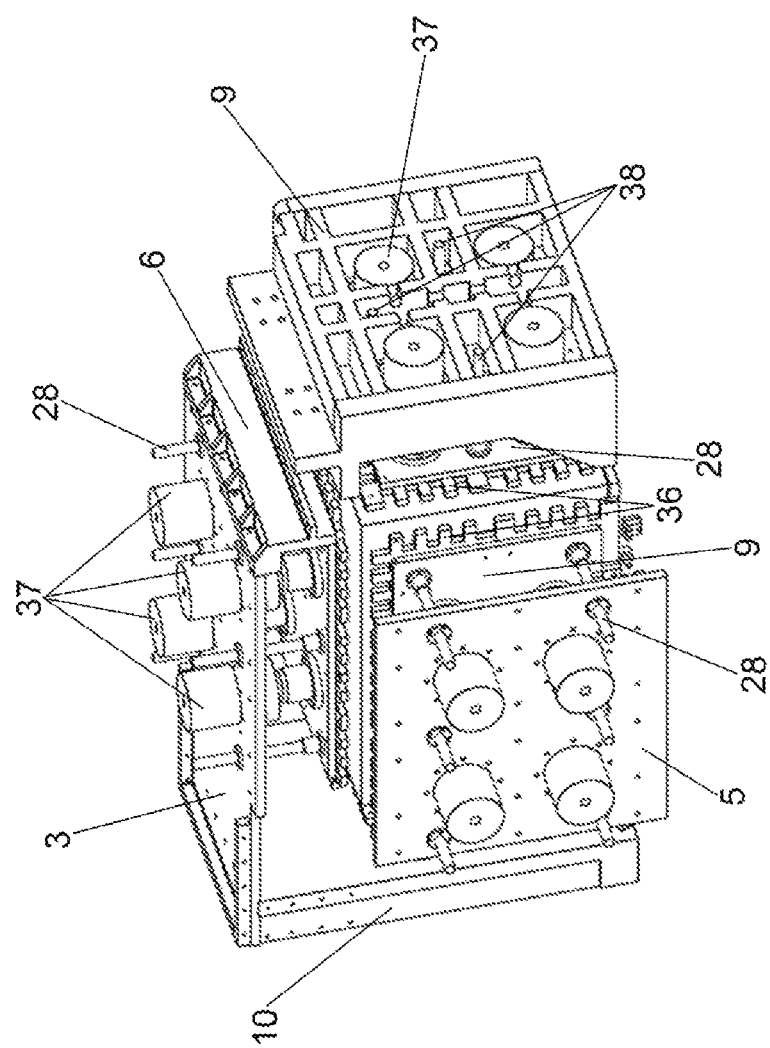
Figure 8:
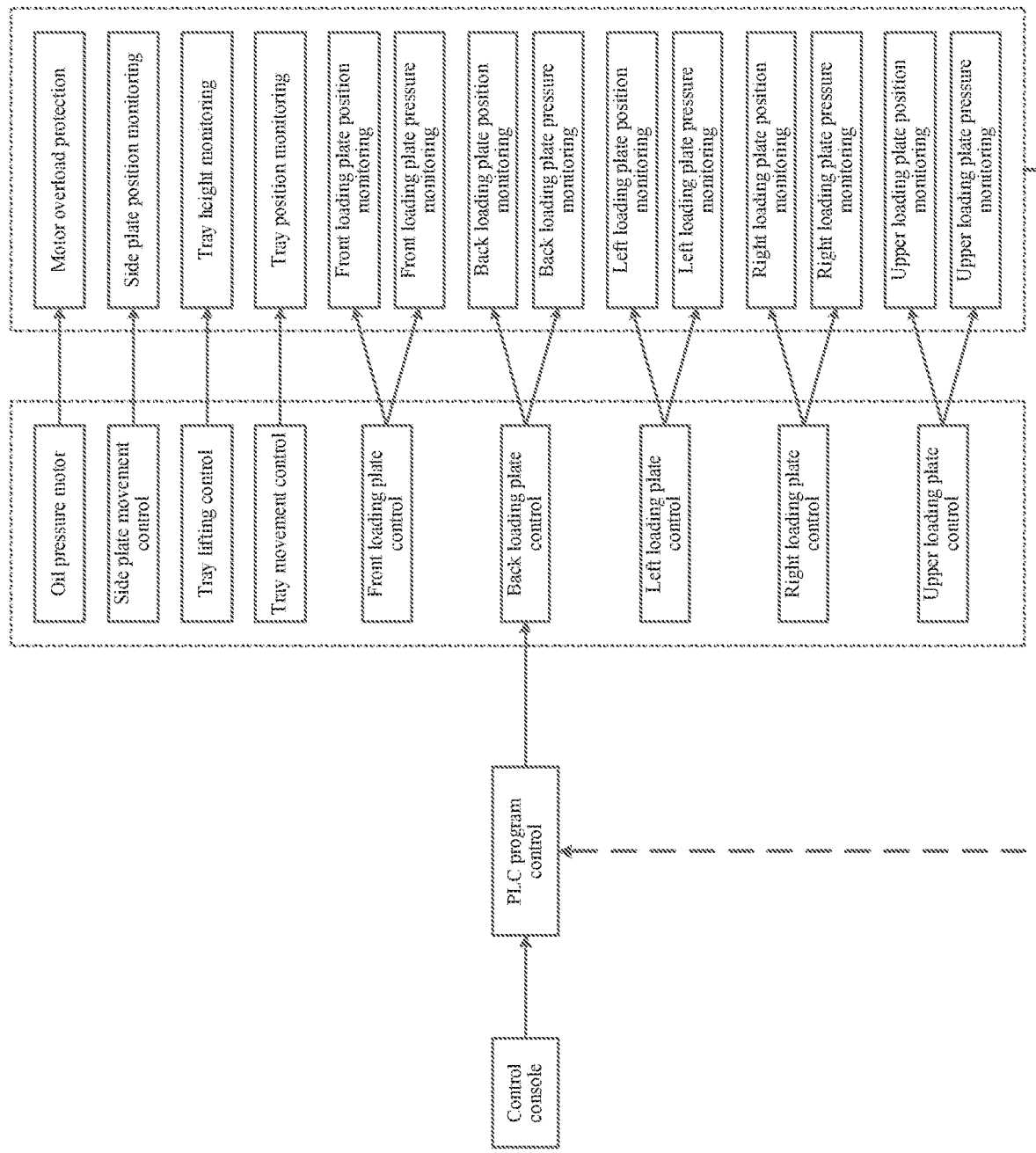
FIG. 8 is a flowchart of a control method of a hydraulic control system in the fully automatic true triaxial tunnel and underground project model test system.
Figure 9:
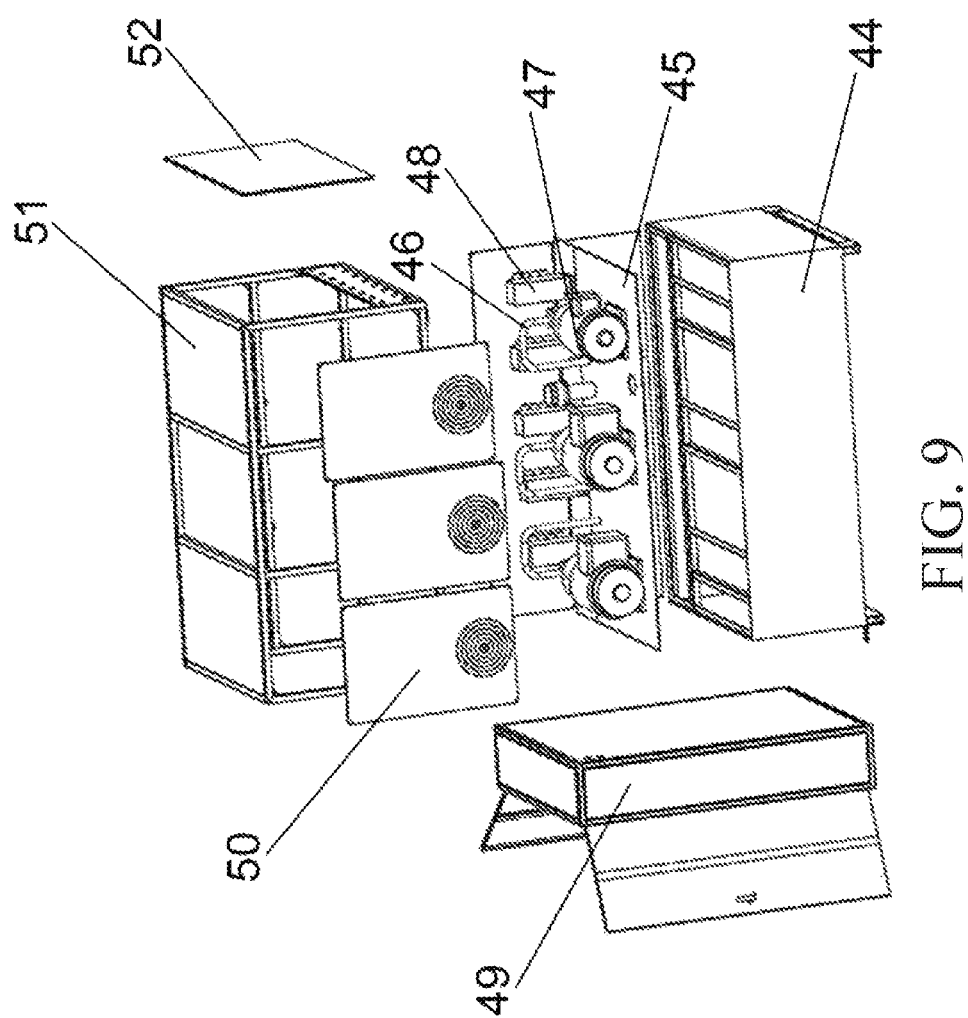
FIG. 9 is a structural schematic diagram of a power system in the fully automatic true triaxial tunnel and underground project model test system.

REFERENCE SIGNS 1 circular arc-shaped outer bracket, 2 switch door bracket, 3 upper main plate, 4 left main plate, 5 right main plate, 6 connection reinforcing member, 7 left reinforcing plate, 8 right reinforcing plate, 9 back main plate, 10 front main plate, 11 rail, 12 pulley, 13 fixing frame, 14 guide rail fixing plate, 15 pulley fixing plate, 16 left moving oil cylinder, 17 oil cylinder fixing bracket, 18 latch pin, 19 tray ejecting plate, 20 pulley,
21 tray, 22 tray bracket, 23 telescopic oil cylinder, 24 latch pin, 25 V-shaped guide rail, 26 pulley,
27 pulley supporting seat, 28 auxiliary plate, 29 lifting oil cylinder, 30 fixing seat, 31 cover plate, 32 guide rail fixing plate, 33 roller, 34 guide rail reinforcing bracket, 35 foot pad bracket, 36 pressure plate, 37 hydraulic jack, 38 force guide rod, 39 model test body, 40 tunnel hole, 41 protective cover, 42 main chassis. 43 auxiliary chassis, 44 oil tank, 45 oil tank cover plate, 16 oil pipe, 47 oil pump, 48 proportional pressure flow control valve, 49 distribution box, 50 back closure plate, 51 upper closure plate, and 52 right closure plate.

DETAILED DESCRIPTION OF THE EMBODIMENTS

It should be noted that the following detailed description is illustrative and is intended to provide further description of the present application. All technical and scientific terms used herein have the same meaning as commonly understood by those of ordinary skill in the art to which the present invention belongs, unless otherwise indicated.

It should be noted that the terms used herein are for the purpose of describing particular embodiments only, and are not intended to limit the exemplary embodiments. As used herein, the singular forms are also intended to include the plural forms, unless the context clearly indicates otherwise, and it should be also understood that, when the terms "include" and/or "comprise" are used in the specification, the terms indicate the presence of features, steps, operations, devices, components, and/or combinations thereof.

As described in the background art, the following problems exist in the prior art:

(1) A part of the model test systems may cause uneven stress of the test pieces due to the defects of loading devices, and unnecessary shear stress on the surfaces of the test pieces, which affects the accuracy and reliability of the test results (2) A part of the model test systems has low loading capacity, such as flexible bladder or hydraulic pillow loading, thereby failing to provide a sufficient load to simulate the high geostress state of deeply buried rock masses.

(3) The model test systems have the disadvantages of being cumbersome, requiring a lot of manpower and material resources, and being unable to achieve automation.

(4) A precursor information monitoring model test system of tunnel water inrush disasters is lacked to clearly clarify the multi-element precursor information of the evolution process of power catastrophe of water inrush of water-rich tunnels and the water inrush disasters, and the present application provides a fully automatic true triaxial tunnel and underground project model test system in order to solve the above-mentioned technical problems.

In a typical embodiment of the present application, as shown in FIG. 1, a fully automatic true triaxial tunnel and underground project model test system is provided, including a hydraulic control system, a power system and a test device system.

The test device system includes a triaxial loading system, a model test piece system, and an automatic data collection and analysis system. The triaxial loading system applies a three-way pressure to the model test piece system; the data collection system is used for collecting change data of various physical variables in an excavation process of a water-rich tunnel; and the model test system is used for simulating the real situation of the water-rich tunnel.

The triaxial loading system includes a test bench, a vertical loading system, horizontal front and back loading systems and horizontal left and right loading systems, the vertical, horizontal front and back, and horizontal left and right loading systems apply the three-way pressure to a model test body to better restore the actual stress state of a rock block; and the test bench functions for supporting and fixing, and providing a counter-force.

The test bench includes a circular arc-shaped outer bracket 1, a chassis and a switch door bracket 2, which are spliced by bolts, so that the test bench is modular and is convenient to disassemble and assemble. The outer bracket 1 is designed in a circular arc shape, thereby having an aesthetic appearance and saving the material, the upper side of the outer bracket 1 is connected with the vertical loading system through an upper main plate 3, and the left and right sides of the outer bracket 1 are respectively connected with the horizontal left-right loading system through a left main plate 4 and a right main plate 5. In order to ensure the overall stability and connectivity of the device, the upper main plate 3 is connected with the switch door bracket 2 through a connection reinforcing member 6, and left and right reinforcing plates 7, 8 are used for connecting the upper main plate 3 and a back main plate 9.

The switch door bracket 2 is connected with a front loading system through a front main plate 10, and the front loading system moves along with the switch door; the two parallel rails 11 are paved above the bracket, a loading truck is arranged above the rails 11, the loading truck is composed of a pulley 12, a fixing frame 13, a guide rail fixing plate 14, a pulley fixing plate 15, a left moving oil cylinder 16 and an oil cylinder fixing bracket 17, the left moving oil cylinder 16 is connected with the switch door bracket 2 through the oil cylinder fixing bracket 17, is connected with the pulley fixing plate 15 through an oil cylinder latch pin 18, and has a function of providing long-term power for the loading truck, the pulley fixing plate 15 is used for fixing the pulley 12 and driving the same to move back and forth along the rail without misalignment, the guide rail fixing plate 14 is connected with the pulley fixing plate 15 through a groove and is used for maintaining the stability of the loading truck, the fixing frame 13 is used for connecting the front main plate 10 with the loading truck and maintaining the integrity of the switch door system, a sensor is arranged on the switch door system and is controlled by a hydraulic control system to control the switch door in real time so as to control the opening amplitude of the switch door.

The chassis is composed of a main chassis 42, two auxiliary chassises 43 and a front extension chassis, which are spliced by bolts. A row of pulleys 20 fixed to a tray ejecting plate 19 are connected to the left and right sides of the main chassis, a tray 21 is placed on the pulleys 20, a tray bracket 22 and a telescopic oil cylinder 23 are arranged below the main chassis and are connected through a tray latch pin 24, and the forward and backward movement of the tray 21 requires the telescopic cylinder 23 to supply energy. Four and one V-shaped guide rails 25 are respectively paved on the upper parts of the auxiliary chassises and the main chassis for providing rails for the left and right loading systems and the back loading system to load the test body, pulleys 26 and pulley supporting seats 27 are arranged on the V-shaped rails 25, and the pulley supporting seats 27 are connected with an auxiliary plate 28 of the loading system by bolts for fixing the pulleys 26 to ensure that the pulleys 26 do not shift. Four grooves 29 are formed in the auxiliary chassis, four lifting oil cylinders 29 are placed in the grooves, the lifting oil cylinders 29 provide power for the up and down movement of the tray 21 through the tray ejecting plate 19, a fixing seat 30 is used for fixing the tray ejecting plate 19, so that the system is more integrated and more stable. The front extension chassis composed of a cover plate 31 and a guide rail fixing plate 32, which are connected together, two rows of rollers 33 are fixed on the inner side of the cover plate 31 for providing rails for the entry and exit of the tray, a guide rail reinforcing bracket 34 is connected between the cover plate 31 and the cover plate 31, so that the overall connection is higher, six food pad brackets 35 are fixed on the lower side of the cover plate 31, and the food pad brackets 35 have the function of preventing the deformation of the structure and reinforcing the integrity of the chassis system.

The vertical, horizontal front and back and the horizontal left and right loading systems are respectively composed of a main plate, an auxiliary plate 28, a pressure plate 36, four hydraulic jacks 37 and a force guide rod 38, the loading systems are controlled by five independent control systems and do not influence each other, loading and unloading of the test body can be completed separately, and the true three-axis is truly simulated. The hydraulic jack 37 and the force guide rod 38 are fixed between the main plate and the auxiliary plate 28, the force guide rod 38 ensures better uniformity of the test body during the loading, the vertical loading system and the horizontal left and right loading systems have six force guide rods 38, and the horizontal front and back loading systems have three force guide rods 38. The pressure plate 36 is made into a zigzag shape, which is a special design for preventing the collision of the loading device. The horizontal back loading system is provided with a tunnel excavation hole.

The model test system includes a model test body 39, the test body is a block having a length of 2.5 m, a width of 2 m and a height of 2 m, the test body 39 is in contact with a triaxial pressurization system through the pressure plate 36, and a plurality of water-bearing masses are arranged in the test body for simulating many types of poor water-bearing masses in a water-rich tunnel, including fault fracture zones, water containing caves, karst pipelines and other types, simulating the catastrophic evolution process of various water inrush types, obtaining the precursor information of different water inrush types, and disclosing different water inrush material energy state transitions and critical characteristics thereof, the model test body can be made in a cast-in-place manner or made by laying prefabricated blocks, a tunnel hole 40 is formed in the middle of the model test body, the maximum diameter of the excavation hole is 200 mm, and an excavation protective cover 41 is arranged at the entrance of the hole for protecting the test system.

The automatic data collection and analysis device includes a micro optical fiber sensor embedded in the model test piece, an optical fiber monitoring system, a micro pressure box and a strain brick, and can collect multi-field information such as model stress, displacement, osmotic pressure and the like, and real-time automatic collection of the information is achieved by a computer program, to achieve real-time data entry, analysis, drawing and early warning processing of multi-physical field information.

The hydraulic control system is monitored and operated by a computer, is connected with the power system and the test device, and achieves the automatic control of the entire test process by a programming algorithm, the core of the control system is a programmable logic controller running on a microcomputer, the execution and operation of various commands are performed by the PLC, and the automatic operation of the loading modules of the power system and the model test bench is realized by a model test control system running in a CPU. The control system can automatically control an oil pump in the power system, and can also automatically control the main plates, the switch door and the tray of the model test bench, and can perform automatic monitoring and real-time feedback on the position of the tray, the loading positions of the main plates, the positions of the auxiliary plates, the position of the switch door and the pressure magnitude. In a test project, the test bench can be automatically operated by inputting preparatory positions and error values of devices into the equipment, and the positions of the devices and the pressure magnitude can be monitored in real time. The hydraulic control system has the advantages of multi-stage loading, constant pressure maintaining, intelligent compensation and real-time monitoring. The control system includes 7 modules of home page return, manual operation, automatic operation, test parameter adjustment, test operation state monitoring, alarm display and system exit.

The manual operation module can adjust the state of the switch door, manually control the ascending, descending, coming-in and going-out states of the tray, and meanwhile can feed back the displayed position and pressure parameters according to the detection. The positions of the loading plates and the required forces to be applied need to be manually filled and set.

In an automatic operation process, the automatic loading module can realize the automatic operation of the test bench by inputting preliminary positions and the error values, monitor the position and pressure parameters of the loading plates in real time and perform window visual dynamic demonstration.

The main function of the test parameter adjustment module is achieving multi-stage loading by using test parameter setting and inputting multiple stages of pressure, loading time, pressure holding time and a running switch, thereby meeting the test requirements and being closer to the actual general project situation.

The test operation state monitoring module mainly monitors the positions and pressures in real time. The monitoring data change state can be visually displayed through a dynamic curve, and the current operation situation is displayed by digits to embody the intuitiveness.

The alarm display module provides automatic feedback on safety error items through the recorded equipment operation state, so that the test personnel can conveniently inspect, repair and maintain the equipment.

The power system is composed of an oil tank 44, an oil tank cover plate 45, an oil pipe 46, an oil pump 47, a proportional pressure flow control valve 48, a distribution box 49, a back closure plate 50, an upper closure plate 51, and a right closure plate 52, the power system is connected with the control system, after the power supply is turned on, the oil pump 44 works to extract the hydraulic oil in the oil tank, the oil is controlled by the proportional pressure flow control valve 45 to enter the hydraulic cylinders to load the test body, and when the test body is unloaded, the hydraulic oil enters the oil tank 44 through the oil pipe 46.

A use method of the fully automatic true triaxial tunnel and underground project model test system includes the following steps:

1. Opening of the switch door: the device is started, the left moving oil cylinder 16 provides power, and the loading truck moves to drive the front main plate 10 so as to open the switch door of the test system.

2. Transportation of the test body: after the switch door is opened, the lifting oil cylinder 29 provides power, the tray 21 is removed from the main chassis through the tray ejecting plate 19 so as to move on the pulley 20, after the tray moves on a fixed position of the front extension chassis, the test body is placed and fixed, and then the tray 21 runs to the designated position in the model test system again, and finally the tray 21 drops and is fixed to the main chassis.

3. The application of an initial stress field: after the tray 21 is fixed, the control system controls the power system, the hydraulic oil enters through the oil pipe 46, the hydraulic jacks in three directions work at the same time to load the test body 39 to simulate the three-way compression of the rock mass. The initial stress field is applied in a multi-stage loading mode, the pressure stabilization after every stage of loading is controlled by the proportional pressure flow control valve 45, and the next stage of loading is achieved after meeting the pressure to be maintained so as to achieve the required initial pressure.

4. Excavation of the test body: after the test body 39 arrives at the required initial stress field, the test body 39 is excavated and is slowly excavated at the water bearing mass, and the test phenomenon is observed from time to time.

5. Capture of multi-element precursor information of the water inrush of the tunnel: the multi-element information includes displacement, stress, pressure and the like and is transmitted by a monitoring element to a data analysis system to perform real-time data entry; analysis, and the like.

6. Execution of multiple groups of tests: the water inrush phenomenon of the tunnel is analyzed through multiple groups of test bodies, and the water inrush phenomenon of the water-rich tunnel is quantitatively described in combination with the data of the real-time data collection system, and precursor information of the water inrush and other rules are summarized through the test phenomenon.

It can be seen from the above descriptions that the embodiment of the present invention provided by the present invention achieves the following technical effects:

(8) The model test system is modular and is convenient to assemble, disassemble and transport.

(9) The whole process of the model test is controlled by a computer, automatic operation is achieved, so that the test is simpler and more convenient, the manpower, material resources and financial resources are greatly saved, and the applicability is better.

(10) The model test system adopts the force guide rods, so that the loading is uniform, the stress of the test piece is uniform, the loading accuracy can reach 0.01%, and the test result is more accurate and reliable.

(11) The model test system has better loading capacity and can simulate the stress state of the deeply buried rock mass, and the maximal simulation buried depth can be greater than 3000 m.

(12) The size of the model test body is 1.5×1.0×1.0 m, so that the size is moderate, the model test body can be cast-in-place and can also be prefabricated to achieve repeated tests.

(13) The model test system realizes the simulation of a complex three-dimensional geostress field via discrete multi-principal stress loading, thereby being more related to the actual situation, and the test result has guiding significance.

(14) The test body can simulate a variety of disaster source water types, thereby enriching a variety of water inrush types and water-rich shapes, and the multi-element precursor information of the water inrush disasters under different disaster source forms can be researched.

(15) Through system software control, independent hydraulic loading of each direction can be achieved.

Although the specific embodiments of the present invention has been described above with reference to the drawings, the protection scope of the present invention is not limited thereto, and those skilled in the art to which the present invention belongs should understand that various modifications or variations, which can made by those skilled in the art on the basis of the technical solutions of the present invention without any creative effect, still fall within the protection scope of the present invention.

The invention claimed is:

1. A fully automatic true triaxial tunnel and underground project model test system, comprising:
   a triaxial loading device for loading a model test piece, comprising: a test bench, a vertical loading system, horizontal front and horizontal back loading systems and horizontal left and horizontal right loading systems, the vertical loading system, the horizontal front and horizontal back loading systems and the horizontal left and horizontal right loading systems apply a three-way pressure to a model test body to restore an actual stress state of a rock block, the test bench functioning for supporting and fixing, and providing a counter-force;
   an automatic data collection and analysis device, comprising: a micro optical fiber sensor embedded in the model test piece, an optical fiber monitoring system, a micro pressure box and a strain brick, the automatic data collection and analysis device configured to collect multi-field information including at least one of model stress, displacement, and osmotic pressure, real-time automatic collection of information being achieved by a computer program to achieve real-time data entry, analysis, drawing and early warning processing of multi-physical field information;
a power system providing required power for a test; and
a control system, intelligently controlling a position and a loading pressure of a loading plate, and controlling automatic opening, closing and extension and retraction of a switch door and a bottom plate.

2. The fully automatic true triaxial tunnel and underground project model test system according to claim 1, wherein:
the test bench comprises a circular arc-shaped outer bracket, an automatic telescopic base bench, and an automatic switch door bracket;
an upper side of the circular arc-shaped outer bracket is connected with the vertical loading system through an upper main plate, a left side and a right side of the outer bracket being respectively connected with the horizontal left- and horizontal right loading systems through a left main plate and a right main plate;
the automatic switch door bracket and the circular arc-shaped outer bracket straddle a chassis, a tray being arranged on the chassis, the tray ascending and descending under a driving of a driving device so as to transport the model test piece to a designated position; and
the automatic switch door bracket comprises the switch door that can automatically open or close under a driving of a power device, the horizontal front loading system being mounted on the switch door, the switch door being connected with the automatic switch door bracket through a front main plate.

3. The fully automatic true triaxial tunnel and underground project model test system according to claim 2, wherein:
the switch door bracket further comprises a structural frame, a loading truck and a power device, a slide rail being arranged on a top of the structural frame, the loading truck being controlled by the power device to slide back and forth along the slide rail;
the loading truck is connected with the switch door through a connecting piece to drive the switch door to slide back and forth, a bottom of the switch door being suspended relative to the structural frame;
a sensor is mounted on the structural frame; and
after the test piece is moved into a simulation test device, the sensor sends a signal to a controller, and the controller controls the power device to control the switch door to automatically close.

4. The fully automatic true triaxial tunnel and underground project model test system according to claim 3, wherein the loading truck comprises a truck body, and the truck body is connected with four rollers through a pulley fixing plate; and
the pulley fixing plate is used for fixing the rollers, a reinforcing block is arranged in the truck body, a fixing frame is mounted at a bottom of the reinforcing block, and the fixing frame is connected with the switch door.

5. The fully automatic true triaxial tunnel and underground project model test system according to claim 3, wherein the slide rail is a V-shaped slide rail and is connected with the structural frame by a hexagonal cylindrical head screw.

6. The fully automatic true triaxial tunnel and underground project model test system according to claim 3, wherein:
the chassis comprises a main chassis, two auxiliary chassises, and a front extension chassis;
the two auxiliary chassises are located on two side faces of the main chassis, the front extension chassis extending along an axial direction of the main chassis;
a loading system is arranged on the main chassis, ascending or descending relative to the main chassis under the driving of a lifting oil cylinder, and achieving coming-in and going-out actions along the slide rail under the driving of a telescopic hydraulic cylinder;
four V-shaped guide rails and one V-shaped guide rails are respectively provided on the two auxiliary chassises and the main chassis for providing rails for the horizontal left and horizontal right loading systems and the horizontal back loading system to load the test body, pulleys and pulley supporting seats being arranged on the V-shaped rails, the pulley supporting seats being connected with an auxiliary plate of the loading system by bolts for fixing the pulleys to ensure that the pulleys do not shift; and
the front extension chassis comprises two cover plates and a guide rail fixing plate, two rows of rollers being fixed on an inner side of the cover plate to form the guide rail, a guide rail reinforcing bracket being connected between the two cover plates to make an overall connection stronger, the guide rail fixing plate being mounted at a top of the front extension chassis, the guide rail fixing plate being used for fixing the guide rail, the loading system being moveable along the guide rail, a reinforcing support for locking the loading system being arranged in the side plate.

7. The fully automatic true triaxial tunnel and underground project model test system according to claim 6, wherein the loading system comprises a tray, and a tray bracket, the tray bracket being mounted on a side face of the tray, connected to the tray by a latch pin, and having a function of stabilizing the tray.

8. The fully automatic true triaxial tunnel and underground project model test system according to claim 7, wherein:
the lifting oil cylinder drives a tray ejecting plate, the tray ejecting plate driving the tray to move up and down;
after the tray moves to a set position, a position of the tray ejecting plate is located by a locating seat;
the locating seat has a function of fixing the position of the tray ejecting plate so that the tray ejecting plate does not move;
the lifting oil cylinder provides power for the ejection of the tray;
a roller is also mounted on an inner side of the tray ejecting plate, the tray being placed on the roller of the tray ejecting plate; and
six foot pad brackets are fixed on the lower side of the cover plate, the foot pad brackets having the function of preventing a deformation of the structure and reinforcing an integrity of the chassis.

9. The fully automatic true triaxial tunnel and underground project model test system according to claim 1, wherein:
the vertical loading system, the horizontal front and horizontal back loading systems, and the horizontal left and horizontal right loading systems are respectively composed of a main plate, an auxiliary plate, a pressure plate, four hydraulic jacks, and a force guide rod, each of the loading systems being controlled by five independent control systems and not influencing each other, a loading and unloading of the test body capable of being completed separately, a true three-axis being truly simulated; and the hydraulic jack and the force guide rod are fixed between the main plate and the auxiliary plate, the force guide rod ensuring more uniform stress of the test body during the loading, a tunnel excavation hole being formed in the horizontal back loading system.

10. The fully automatic true triaxial tunnel and underground project model test system according to claim 1, wherein:

the model test body is in contact with a triaxial pressurization system through the pressure plate, a plurality of water-bearing masses being arranged in the test body for simulating many types of poor water-bearing masses in a water-rich tunnel, simulating a catastrophic evolution process of various water inrush types, obtaining precursor information of different water inrush types, and disclosing different water inrush material energy state transitions and critical characteristics thereof, the model test body capable of being made in a cast-in-place manner or made by laying prefabricated blocks, a tunnel hole being formed in the middle of the model test body, an excavation protective cover arranged at an entrance of the tunnel hole for protecting the test system.

* * * * *